(12) United States Patent
Bourne

(10) Patent No.: US 7,742,575 B2
(45) Date of Patent: Jun. 22, 2010

(54) MULTI-LEAF COLLIMATOR

(75) Inventor: Duncan Neil Bourne, Redhill (GB)

(73) Assignee: Elekta AB (publ), Stockholm (SE)

( * ) Notice: Subject to any disclaimer, the term of this patent is extended or adjusted under 35 U.S.C. 154(b) by 1 day.

(21) Appl. No.: 12/370,001

(22) Filed: Feb. 12, 2009

(65) Prior Publication Data
US 2009/0207975 A1     Aug. 20, 2009

(30) Foreign Application Priority Data
Feb. 15, 2008   (GB) ................................. 0802762.5

(51) Int. Cl.
G21K 1/04    (2006.01)
(52) U.S. Cl. ...................................................... 378/152
(58) Field of Classification Search ......... 378/147–153; 250/505.1
See application file for complete search history.

(56) References Cited
FOREIGN PATENT DOCUMENTS

| EP | 0 314 214 B1 | 10/1988 |
|---|---|---|
| WO | WO 2007/003925 A2 | 1/2007 |
| WO | WO 2007/124248 A2 | 11/2007 |

Primary Examiner—Courtney Thomas
(74) Attorney, Agent, or Firm—Westman, Champlin & Kelly, P.A.; Z. Peter Sawicki

(57) ABSTRACT

A multi-leaf collimator for use in a radiotherapeutic apparatus comprises a plurality of elongate narrow leaves arranged side-by side and supported in a frame, the frame having upper and lower formations for guiding each leaf into which extend ridges on the upper and lower edges of the leaves, thereby to allow the leaves to move in a longitudinal direction, the upper and lower formations being aligned so that the sides of the leaves when fitted are at a non-zero angle to the beam direction, the upper and lower ridges being located on the upper and lower edges of the leaves so that a line joining their centres is at a non-zero angle to the sides of the leaf, tilted relative to the sides in a sense opposite to that of the beam. An outer face of the upper and/or lower ridges can be aligned with a side face of the leaf, for ease of manufacture. A radiotherapeutic apparatus is also disclosed, comprising a source of radiation and a multi-leaf collimator for shaping the radiation emitted by the source, the multi-leaf collimator being as set out above.

12 Claims, 5 Drawing Sheets

MULTI-LEAF COLLIMATOR

CROSS-REFERENCE TO RELATED APPLICATION

The present application claims priority of British patent application Serial No. 0802762.5, filed Feb. 15, 2008, and published in English the content of which is hereby incorporated by reference in its entirety.

FIELD OF THE INVENTION

The present invention relates to a multi-leaf collimator.

BACKGROUND ART

External Beam Radiotherapy involves the production of a beam of ionising radiation, usually x-rays or a beam of electrons or other sub-atomic particles, which is then directed towards a cancerous region of the patient. This adversely affects the tumour cells, causing an alleviation of the patient's symptoms. Generally, it is preferred to delimit the radiation beam so that the dose is maximised in the tumour cells and minimised in healthy cells of the patient, as this improves the efficiency of treatment and reduces the side effects suffered by a patient. A variety of methods of doing so have evolved.

One principal component in delimiting the radiation dose is the so-called "multi-leaf collimator" (MLC). This is a collimator which consists of a large number of elongate thin leaves arranged side to side in an array. Each leaf is moveable longitudinally so that its tip can be extended into or withdrawn from the radiation field. The array of leaf tips can thus be positioned so as to define a variable edge to the collimator. All the leaves can be withdrawn to open the radiation field, or all the leaves can be extended so as to close it down. Alternatively, some leaves can be withdrawn and some extended so as to define any desired shape, within operational limits. A multi-leaf collimator usually consists of two banks of such arrays, each bank projecting into the radiation field from opposite sides of the collimator. An example of an MLC is shown in EP-A-0,314,214.

WO 2007/124248 shows an MLC with leaves having ridges along their upper and lower edges, to engage in corresponding formations in a leaf support structure. However, this document teaches that the leaves should be aligned relative to the radiation source, i.e. that the sides of the leaf are aligned with the local direction of the radiation.

WO 2007/003925 also shows an MLC leaf having ridges along its upper and lower edges, to engage in corresponding formations in a leaf support structure, but is silent as to the orientation of the leaf relative to the beam.

One factor in the design of a high-quality MLC is the leakage of radiation through the collimator. One likely area for leakage is between the leaves; there must obviously be some degree of separation between the leaves in order to allow them to slide easily relative to the adjacent leaf, and this small gap could allow for leakage. To alleviate this, MLC leaves and their supporting structures can be designed so that the leaves are held at a small acute angle to the beam direction. This means that from the point of view of the beam, the gap between adjacent leaves is closed.

SUMMARY OF THE INVENTION

The present invention provides a multi-leaf collimator for collimating a beam of a radiotherapeutic apparatus, comprising a plurality of elongate narrow leaves arranged side-by side and supported in a frame, the frame having upper and lower formations for guiding each leaf into which extend ridges on the upper and lower edges of the leaves, thereby to allow the leaves to move in a longitudinal direction, the upper and lower formations being aligned so that the sides of the leaves when fitted are at a non-zero angle to the beam direction, the upper and lower ridges being located on the upper and lower edges of the leaves so that a line joining their centres is at a non-zero angle to the sides of the leaf, tilted relative to the sides in a sense opposite to that of the beam.

The upper formations and/or the lower formations can comprise channels into which the ridges extend. Given that there will need to be a number of adjacent channels to accept a plurality of adjacent leaves, each channel can be defined between a pair of ridges.

An outer face of the upper and/or lower ridges can be aligned with a side face of the leaf, for ease of manufacture.

The present invention further comprises a radiotherapeutic apparatus comprising a source of radiation and a multi-leaf collimator for shaping the radiation emitted by the source, the multi-leaf collimator being as set out above.

BRIEF DESCRIPTION OF THE DRAWINGS

An embodiment of the present invention will now be described by way of example, with reference to the accompanying figures in which.

DETAILED DESCRIPTION OF THE EMBODIMENTS

In this description the terms "up" and "down" refer to directions relative to the general disposition of the leaf or leaves of the multi-leaf collimator (MLC). Usually, the rest position for the radiation source of a typical oncology device is at the top of its rotational sweep, and therefore the conventional view of a radiotherapy head is with the beam travelling vertically downward. The leaves will thus be aligned in a generally vertical direction, with their long axis arranged horizontally.

As the radiation head rotates around a patient, as is commonly done in order to irradiate the tumour from a variety of directions and thereby minimise the dose that is applied to healthy tissue, the absolute orientation of the leaves (etc) will of course change, relative to a fixed frame of reference such as the room in which the apparatus is located. However, regardless of the actual orientation of the MLC and its leaves, in this description "up" is intended to mean a direction towards the radiation source, and other directions should be interpreted accordingly.

Figure 1:
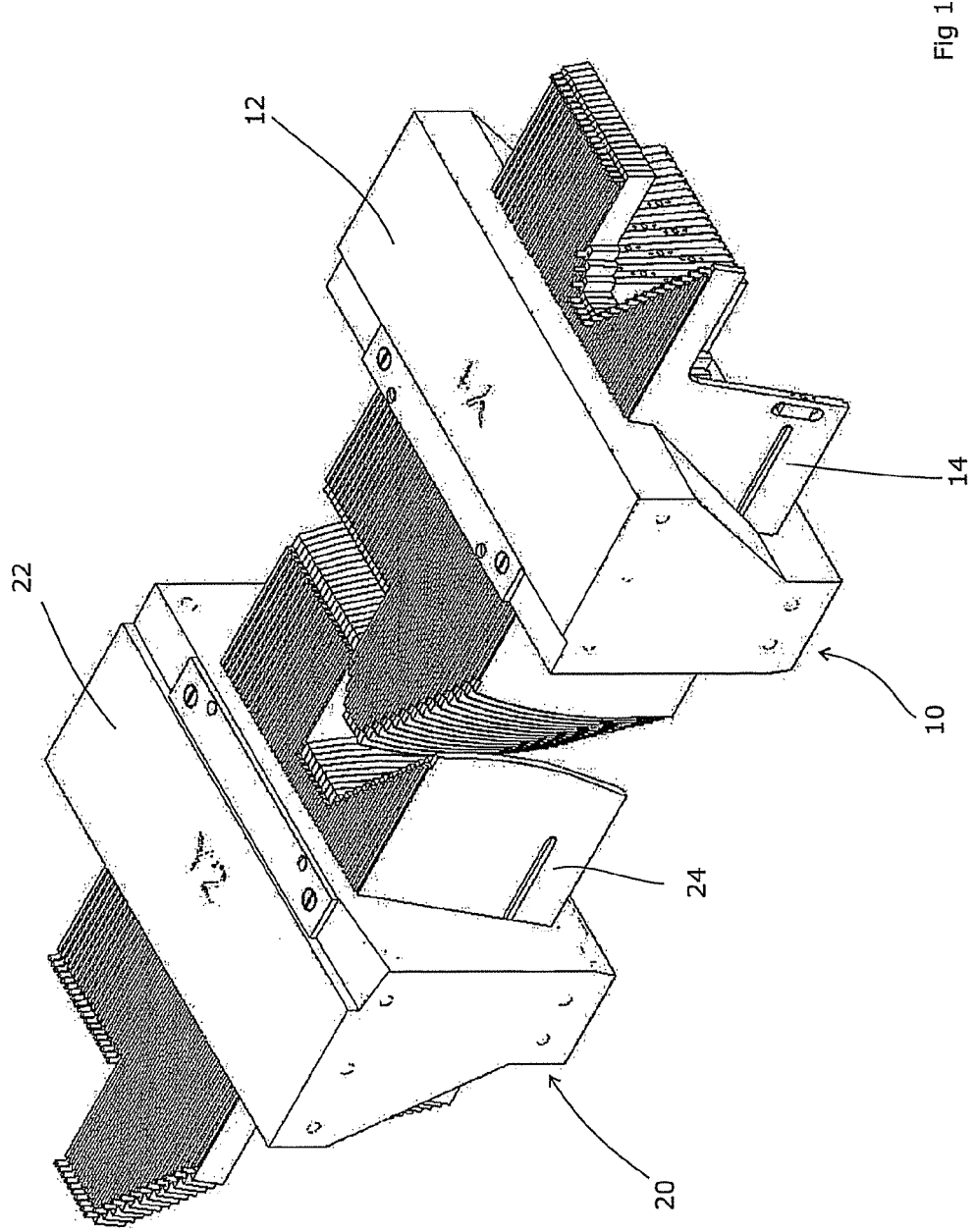
FIG. 1 is a perspective view of a multi-leaf collimator according to the present invention.

FIG. 1 shows an MLC according to the present invention. Two banks of leaves are provided, each facing the other, one on either side of the beam so as to delimit the beam from opposing sides. Thus, a first bank 10 comprises a frame 12 which supports an array of leaves 14, whilst a second bank 20 comprises a frame 22 which supports an array of leaves 24.

Each leaf is oriented in a generally upright manner relative to the beam, with most leaves having a small deflection from perfect verticality as will be described shortly. The leaves 14, 24 are held in the frames 12, 22 by ridges running the length of the upper and lower edges of the leaves, which engage in corresponding channels in the frames so that the leaves can slide horizontally backwards (i.e. out of the beam) and forwards (i.e. into the beam). Each leaf is driven by a suitable motor or other drive means (not illustrated) in a generally known manner.

Figure 2:
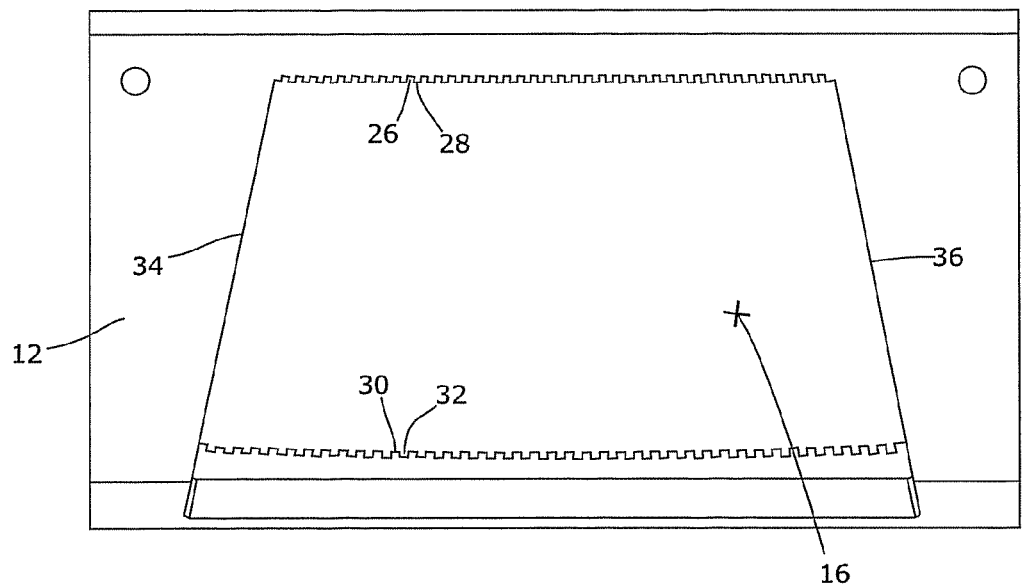
FIG. 2 shows the leaf guide, viewed along the longitudinal direction of a leaf.

FIG. 2 shows the frame 12 of the first bank, which supports the leaves 14. The other frame 22 is substantially identical to this frame, albeit a mirror image thereof. The frame 12 is shown in FIG. 2 from a point of view along the long axis of the leaves 14, with the leaves themselves absent. An aperture 16 is formed within the frame 12 to receive the leaves 14, and has a corrugated upper edge 18 in which a series of small channels 26 are defined between frame ridges 28. Each channel 26 receives a leaf ridge running along the upper edge of the leaf 14; the leaf ridges are narrower than the leaf itself so as to allow space for the frame ridges 28 which define each channel 26, whilst still maintaining a very small separation between each leaf 14. A corresponding array of frame ridges 30 that define channels 32 between them is provided on the bottom edge of the aperture 16.

The ridges 28 on the upper edge of the aperture 16 are more closely spaced than the ridges 30 on the bottom edge, and the side faces 34, 36 of the aperture 16 angle outwardly downwards. This allows the leaves 14 to be held in a non-parallel state, with the vertical axes of the leaves converging upwards towards a single convergence point. As a result, the divergent radiation beam emanating from the beam source can be collimated by the leaves with a minimal penumbra.

Figure 3:
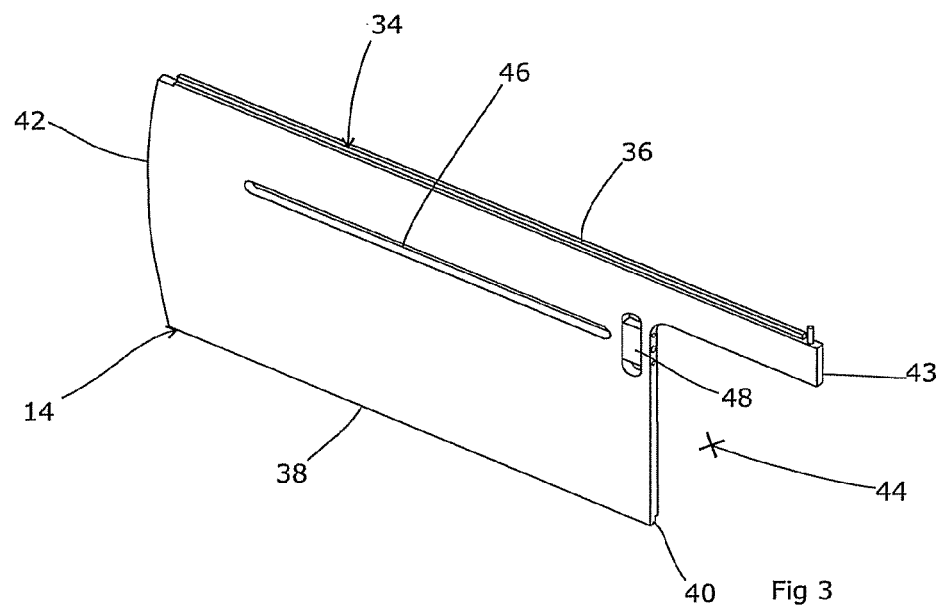
FIG. 3 shows a perspective view of a single leaf.

FIG. 3 shows a single leaf 14. This has an elongate upper edge 34 along which is provided a ridge 36. An elongate lower edge 38 has a corresponding ridge 40. A front edge 42 projects into the radiation beam and is gently curved so that the penumbra is minimised regardless of the translational position of the leaf. A rear edge 43 has an inset area 44 to accommodate the drive mechanism, which is by way of a rotatable threaded rod (not shown) which passes into an elongate aperture 46 running along a substantial portion of the length of the leaf, accessed via an internally threaded section 48 which engages with the threaded rod. Thus, as the threaded rod is rotated, it drives the threaded section 48 and hence the leaf 14.

Figure 4:
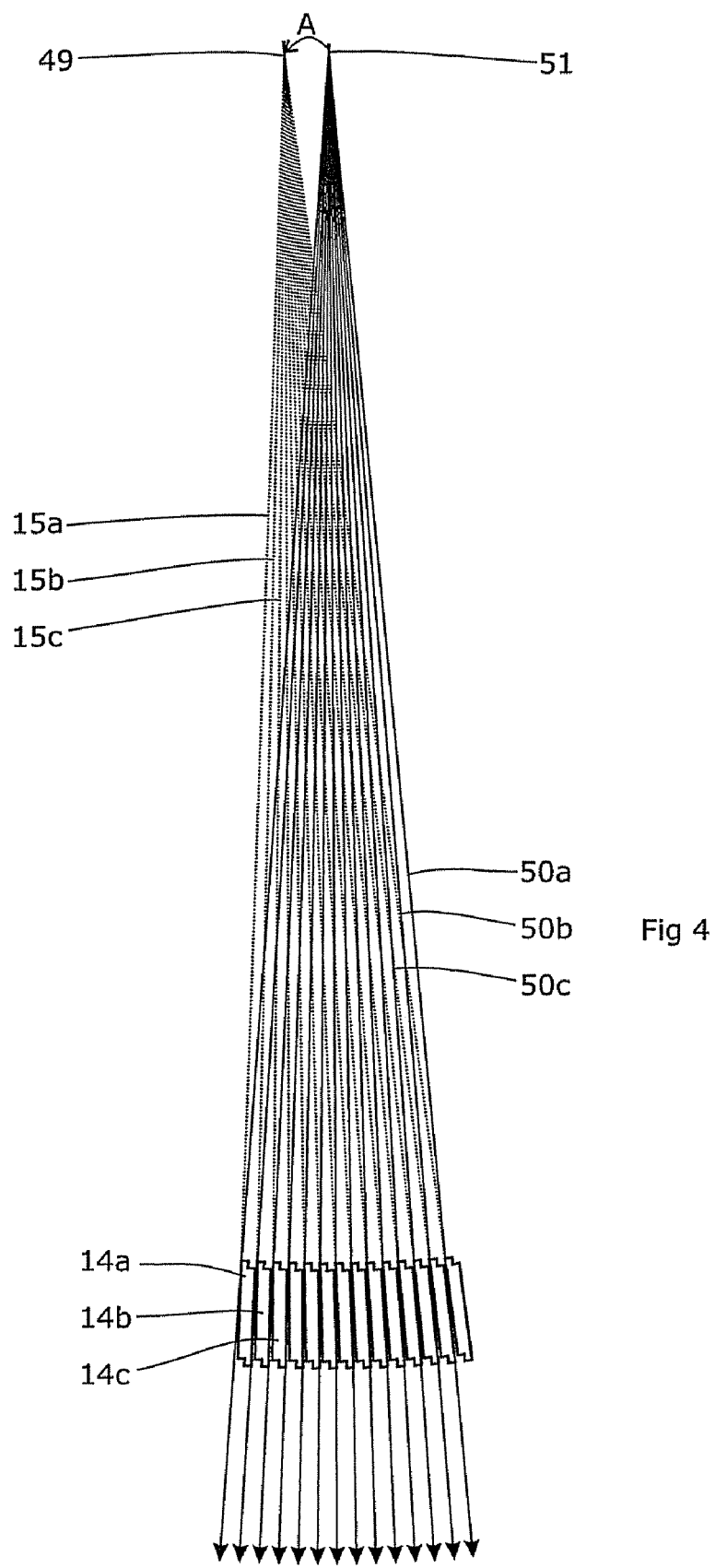
FIG. 4 shows the alignment of the leaves relative to the radiation source.

FIG. 4 illustrates the alignment of the leaves relative to the radiation source. A set of leaves 14a, 14b, 14c etc are shown, together with a plurality of rays 50a, 50b, 50c etc all of which emanate from the radiation source 51. In practice, of course, the radiation emitted by the source is continuous over the field of illumination, rather than being in the form of discrete narrow rays as illustrated for the purposes of clarity. FIG. 4 also shows a series of lines 15a, 15b, 15c etc which show the alignment of a side of each leaf 14a, 14b, 14c etc. These converge on a point 49 which is set so as to be at the same height as the radiation source 51, but offset slightly therefrom as shown by arrow A. The result is that the radiation beams strike the leaves 14 at a slight angle, thereby avoiding the creation of a thin gap between each leaf through which radiation could pass uninterrupted.

Figure 5:
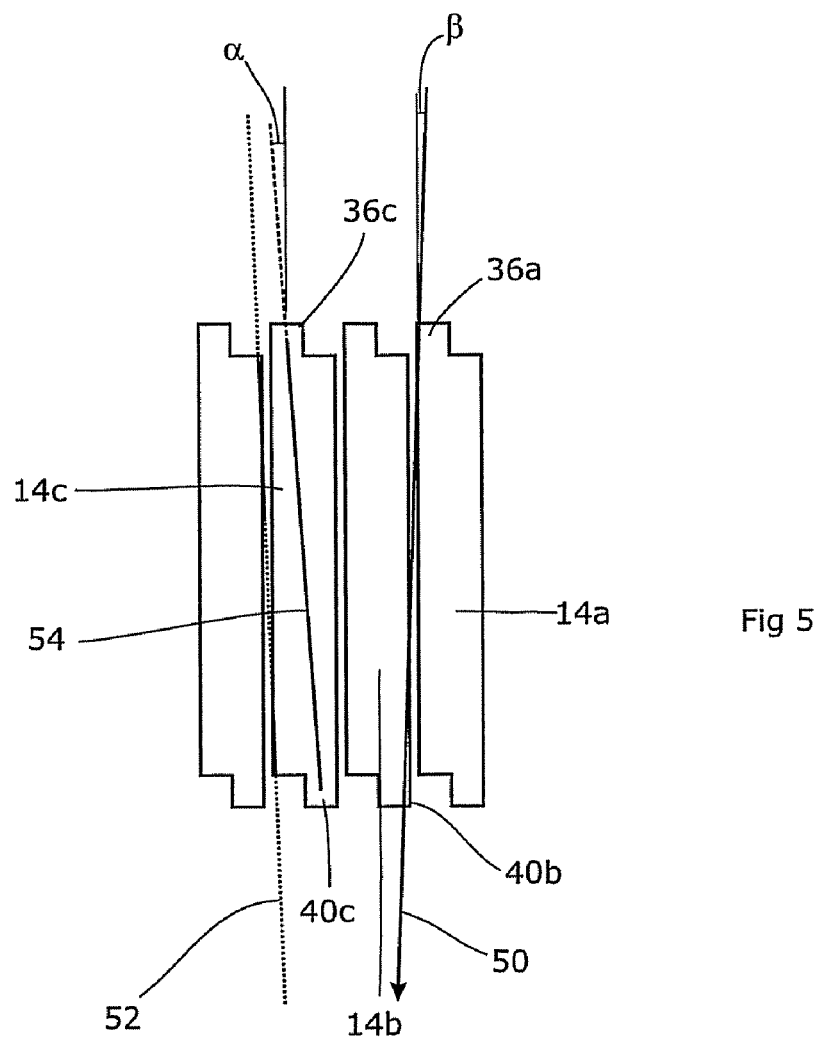
FIG. 5 shows the arrangement of a leaf relative to the beam direction.

FIG. 5 shows a subset of the leaves 14, side by side, together with an individual beam segment 50. As mentioned earlier, the beam 50 is not perfectly parallel to the vertical extent of the leaves 14, in order to minimise the leakage between leaves. However, FIG. 5 illustrates a worst case scenario in which the beam just impinges upon the upper edge of a first leaf 14a and the lower edge of a second leaf 14b, and otherwise passes through the gap between them to the maximum extent possible. It therefore passes for much of its path between the two leaves and hence demonstrates the beam path of minimum attenuation that is possible with this design of MLC. It should be noted that the gaps between the leaves, the thicknesses of the leaves, and the angle of the beam 50 are exaggerated in order to demonstrate the effect more clearly.

It will be seen that in this example the beam 50 intersects with and is attenuated by both the upper ridge 36a of the leaf 14a and the lower ridge 40b of the leaf 14b. As a result, the attenuation of this worst-case beam 50 is maximised through careful location of the leaf ridges. Line 52 shows a hypothetical alternative beam 52, in which the relative tilt of the MLC to the beam direction is reversed, hence enabling the beam to miss the upper ridges 36 and the lower ridges 40 and thereby suffer slightly less attenuation. Accordingly, the leakage rate through such a hypothetical MLC would be greater than the leakage rate of the MLC here described.

It can be seen from FIG. 5 that a beam just to the right of the illustrated beam 50 may just miss the lower ridge 40b. However, this beam will meet a greater length of the upper ridge 36a and the leaf 14a. Careful design of the dimensions of the leaves and the ridges can ensure that beams will always pass through either the whole of the upper ridge, or the whole of the lower ridge, or a combination of the two that adds up (in total) to the attenuation of one ridge, but never more or less than the equivalent attenuation of one ridge. This means that the leakage profile of the MLC as a whole is smoother (as well as lower) than the leakage profile of an MLC where beams can pass through the leaf without meeting either the upper or the lower ridge.

Likewise, if the chosen inclination of the beam relative to the leaves is lesser, then by careful design of the depths and thicknesses of the upper and lower ridges 36 and 40 relative to the general dimensions of the leaves and the gaps therebetween, it is possible to ensure that the beam 50 will always go through either 36a or 40a (or both) but never none.

These mean that the leakage profile of the MLC as a whole is smoother than if a beam could pass through the leaf without touching either 36a or 40a. Line 54 has been shown in FIG. 5, joining the centre of the upper ridge 36c of one leaf and the lower ridge 40c of that leaf. It will be seen that, since the upper ridges 36 are offset to one side and the lower ridges 40c are offset to the other side of the leaf 14c, the line 54 joining their centres is likewise offset relative to the vertical extent of the leaf 14c. It will be noted that, in FIG. 5, the angle of offset of α of the line 54 joining the centres of the upper ridges 36c and lower ridges 40c is in a direction opposite to the angle offset β between the local direction of the beam 50 and the vertical extent of the leaves 14. That reversal of the sense of the two angles means that the beam 50 suffers greater attenuation even in the worst-case example illustrated. Where the sense of the offset is the same as, for example, between line 54 and line 52, attenuation is less in this worst-case instance. Accordingly, the overall performance of the MLC in terms of the contrast between areas where the beam is being permitted to pass and areas where it should be blocked, is greater.

Figure 5A:
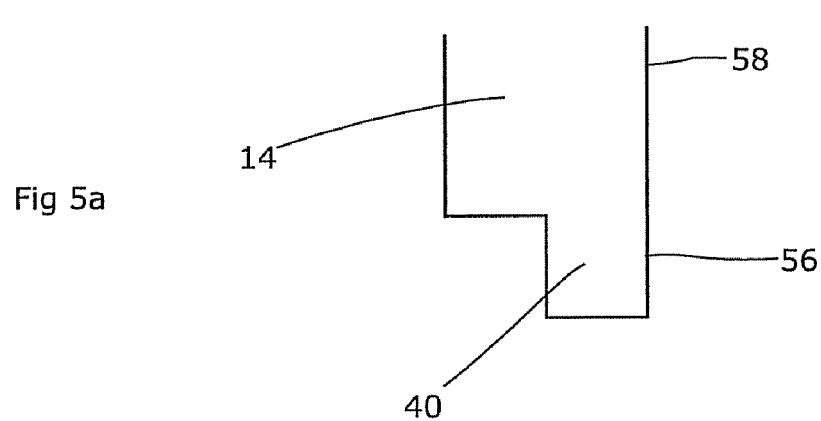

FIG. 5 illustrates our preferred arrangement. The upper ridges 36 and the lower ridges 40 are fully offset to one side of the leaf, i.e. the sides 56 of the ridges are smooth with the sides 58 of the leaf, with no ridge or undulation present. This maximises the attenuation of a worst-case beam 50. FIG. 5a illustrates this. However, it is still possible to design leaves that take advantage of this principle and have some advantage over existing leaves, albeit not as great an advantage as the arrangement shown in FIG. 4.

Figure 6:
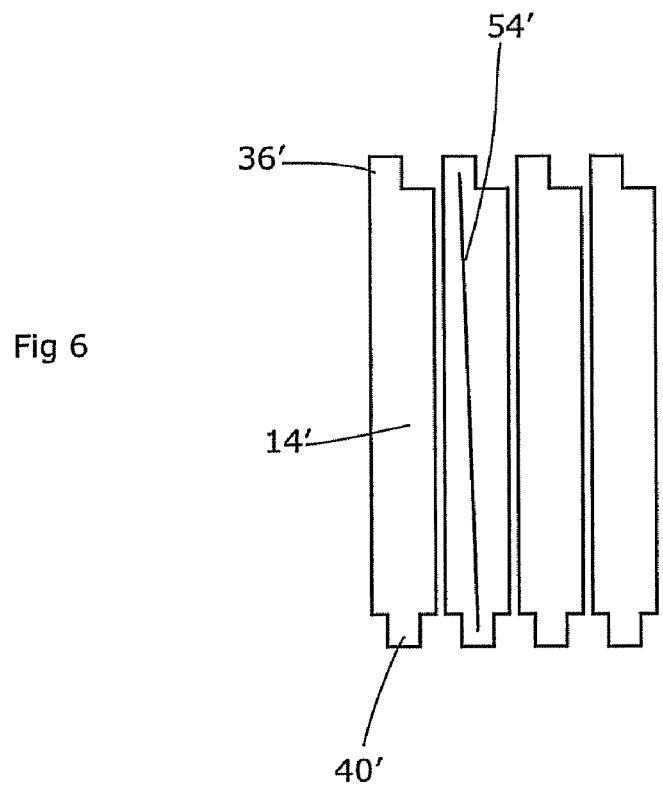
FIG. 6 shows an alternative design of leaf.

FIG. 6 illustrates such a set of leaves 14'. The upper ridge 36' has an edge that is smooth with the relevant side of the leaf 14', but the lower ridge 40' is centrally placed relative to the leaf. The line 54' joining the centres of these ridges 36' and 40' is again tilted, although the angle of that tilt relative to the leaves 14 is less than the angle = in FIG. 4. Nevertheless, some greater attenuation will be offered by such leaves 14'.

Figure 7:
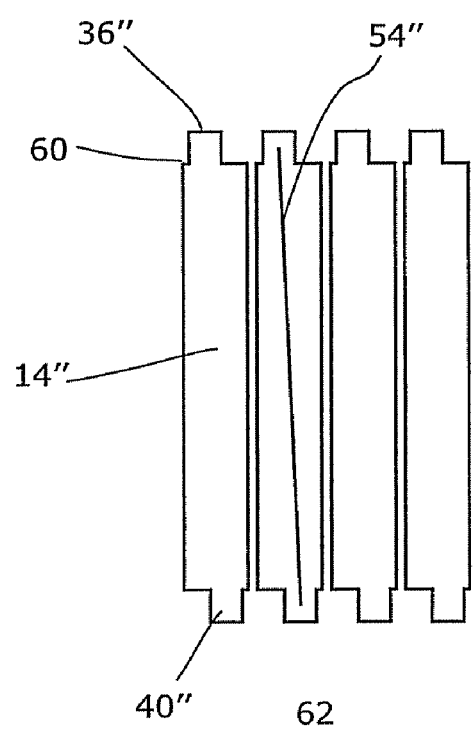
FIG. 7 shows a further alternative design of leaf.

FIG. 7 shows a further alternative version of the leaves 14". In this case, both the upper ridges 36" and the lower ridges 40" are offset slightly from the sides of the leaf 14" and there will be a small step 60, 62 between them. However, a line 54" joining the centres of the upper ridges 36" and the lower ridges 40" is still inclined slightly although again the angle of inclination is less than α.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A multi-leaf collimator for collimating a beam of a radiotherapeutic apparatus, comprising a plurality of elongate narrow leaves arranged side-by side and supported in a frame, the frame having upper and lower formations for guiding each leaf and ridges which extend into the leaves on the upper and lower edges of the leaves, thereby to allow the leaves to move in a longitudinal direction, the upper and lower formations being aligned so that the sides of the leaves when fitted are at a non-zero angle to the beam direction, the upper and lower ridges being located on the upper and lower edges of the leaves so that a line joining their centres is at a non-zero angle to the sides of the leaf, tilted relative to the sides, opposite to that of the beam.

2. The multi-leaf collimator according to claim 1 in which the upper formations comprise channels into which the ridges extend.

3. The multi-leaf collimator according to claim 1 in which the lower formations comprise channels into which the ridges extend.

4. The multi-leaf collimator according to claim 2 in which the channels are defined between a pair of ridges.

5. The multi-leaf collimator according to claim 1 in which an outer face of the upper ridges is aligned with a side face of the leaf.

6. The multi-leaf collimator according to claim 1 in which an outer face of the lower ridges is aligned with a side face of the leaf.

7. A radiotherapeutic apparatus, comprising;
a source of radiation, and
a multi-leaf collimator for shaping the radiation emitted by the source,
the multi-leaf collimator comprising a plurality of elongate narrow leaves arranged side-by side and supported in a frame, the frame having upper and lower formations for guiding each leaf and ridges which extend into the leaves on the upper and lower edges of the leaves, thereby to allow the leaves to move in a longitudinal direction, the upper and lower formations being aligned so that the sides of the leaves when fitted are at a non-zero angle to the beam direction, the upper and lower ridges being located on the upper and lower edges of the leaves so that a line joining their centres is at a non-zero angle to the sides of the leaf, tilted relative to the sides in a sense opposite to that of the beam.

8. The radiotherapeutic apparatus according to claim 7 in which the upper formations comprise channels into which the ridges extend.

9. The radiotherapeutic apparatus according to claim 7 in which the lower formations comprise channels into which the ridges extend.

10. The radiotherapeutic apparatus according to claim 8 in which the channels are defined between a pair of ridges.

11. The radiotherapeutic apparatus according to claim 7 in which an outer face of the upper ridges is aligned with a side face of the leaf.

12. The radiotherapeutic apparatus according to claim 7 in which an outer face of the lower ridges is aligned with a side face of the leaf.

* * * * *